(12) United States Patent
Hochleitner et al.

(10) Patent No.: US 7,067,307 B2
(45) Date of Patent: Jun. 27, 2006

(54) BIOARTIFICIAL DEVICE FOR THE STORAGE, CULTIVATION AND/OR MULTIPLICATION OF CELLS

(75) Inventors: Boris-Wolfgang Hochleitner, Graz (AT); Paul Hengster, Innsbruck (AT)

(73) Assignee: Raimung Margreiter, Seefeld (AT)

( * ) Notice: Subject to any disclaimer, the term of this patent is extended or adjusted under 35 U.S.C. 154(b) by 0 days.

(21) Appl. No.: 10/641,275

(22) Filed: Aug. 14, 2003

(65) Prior Publication Data

US 2004/0033593 A1 Feb. 19, 2004

Related U.S. Application Data

(63) Continuation of application No. PCT/AT02/00045, filed on Feb. 11, 2002.

(30) Foreign Application Priority Data

Feb. 14, 2001 (EP) .................................. 01103420

(51) Int. Cl.
*C12M 3/06* (2006.01)

(52) U.S. Cl. ................ 435/297.2; 435/297.3; 435/298.2; 422/48; 210/321.64; 210/321.68; 210/321.74

(58) Field of Classification Search ............ 435/297.2, 435/297.3, 297.5, 298.2, 295.3; 422/48; 210/646, 321.64, 321.68, 321.67, 321.74, 210/321.78, 321.8

See application file for complete search history.

(56) References Cited

U.S. PATENT DOCUMENTS

| | | | |
|---|---|---|---|
| 3,734,851 A * | 5/1973 | Matsumura | ............ 210/632 |
| 4,242,459 A | 12/1980 | Chick et al. | |
| 4,242,460 A | 12/1980 | Chick et al. | |
| 4,323,457 A | 4/1982 | Sun et al. | |
| 4,649,114 A | 3/1987 | Miltenburger et al. | |
| 4,808,378 A * | 2/1989 | Nakanishi et al. | ............ 422/48 |
| 5,026,650 A * | 6/1991 | Schwarz et al. | ......... 435/297.1 |
| 5,043,260 A | 8/1991 | Jauregui | |
| 5,064,764 A | 11/1991 | Besnainon et al. | |
| 5,081,035 A * | 1/1992 | Halberstadt et al. | ..... 435/297.4 |
| 5,155,035 A * | 10/1992 | Schwarz et al. | ............ 435/394 |
| 5,605,835 A | 2/1997 | Hu et al. | |
| 5,712,154 A * | 1/1998 | Mullon et al. | ........... 435/297.4 |
| 5,827,729 A | 10/1998 | Naughton et al. | |
| 6,008,049 A | 12/1999 | Naughton et al. | |

OTHER PUBLICATIONS

Author unknown: "Controlled-Turbulence Bioreactors", NTIS Tech Notes, Mar. 1, 1990, p. 294.*

* cited by examiner

*Primary Examiner*—William H. Beisner
(74) *Attorney, Agent, or Firm*—Laurence A. Greenberg; Werner H. Stemer; Ralph E. Locher (57) ABSTRACT

The bioartificial reactor has a reactor vessel. A cell culture chamber in the reactor, in particular for liver cells, is divided off from a flow chamber for a nutritive medium and from a flow chamber for plasma and blood by semipermeable walls. At least one flow chamber is formed as a tube that is helically wound in the shape of a screw and that is made of semipermeable material.

50 Claims, 6 Drawing Sheets

BIOARTIFICIAL DEVICE FOR THE STORAGE, CULTIVATION AND/OR MULTIPLICATION OF CELLS

CROSS-REFERENCE TO RELATED APPLICATION

This application is a continuation of copending International Application No. PCT/AT02/00045, filed Feb. 11, 2002, which designated the United States and which was not published in English.

BACKGROUND OF THE INVENTION

Field of the Invention

The invention relates to a bioartificial device for storing, cultivating, and/or multiplying cells, in particular liver cells. The device has a reactor vessel in which a cell culture chamber is separated by semipermeable walls on one side from a throughflow chamber for a nutrient medium and on the other side from a throughflow chamber for a body substance, in particular plasma or blood.

Examples of devices with a throughflow chamber for the cultivation of cells, for example islet cells or similar, are shown in the U.S. Pat. Nos. 4,242,460; 4,323,457; and 4,649,114. In all three devices, the throughflow chamber is formed by a coiled tube or the like.

Examples of devices and systems of the type mentioned at the outset with two throughflow chambers, which can be used as bioartificial livers, are shown in U.S. Pat. Nos. 5,043,260; 5,605,835; 5,827,729; and 6,008,049.

Bioreactors with two throughflow chambers allow the storage, cultivation and multiplication of all cells or tissues of all types. This makes possible on the one hand conditions with cell-cell contacts (random collisions), but on the other hand the exchange of substances at the cell surfaces. Such conditions can be advantageous for the most varied cells, in particular for cells with unlimited cell division (stem cells), and allow cultivation and multiplication without a time limit. The provision of two separate perfusion circuits through the reactor vessel makes it possible to feed and supply nutrient substrates or oxygen via one circuit, and simultaneously or intermittently remove synthesis products of the cells or carry out an exchange of substances with the patent via the other circuit, as is required within the framework of a bioartificial liver. However, a metabolic product or synthesis product could also be removed from the reactor vessel to obtain a substance, for example if bacteria cells are cultivated which generate a specific product.

To cultivate cells within the framework of cell expansion, a separate supply of various substances can also be made possible via the two circuit systems. For example a basal nutrient medium is supplied via the first circuit, and a growth factor or differentiation factor supplied or a product removed continuously or intermittently at the same or a different speed, through different membrane types if required, as can be necessitated by a different penetration behaviour, via the second circuit. The supply of gases (oxygen) separated from the medium can also take place via the second circuit.

Devices with liver function are intended to be capable of temporarily assuming the liver function of a patient, in particular in the case of one of the following diseases:

Acute liver failure (fulminant infectious hepatitis, intoxications such as amanita poisoning, etc.)

Primary non-function of a liver transplant

Bridging until liver transplantation in the case of sudden deterioration of a chronic liver disease Intermittent treatment in the case of chronic liver insufficiency.

Acute liver failure is a constellation of clinical symptoms which result from a sudden liver breakdown (Hoofnagle). According to the definition, hepatic encephalopathy, coagulopathy and icterus must be present. In many cases, however, cerebral oedema, kidney failure and finally multiple organ failure also occur. Depending on the etiology, different symptoms can predominate. For example it is known that in the case of paracetamol poisoning, encephalopathy and serious coagulopathy occur with only mild icterus, whereas a fulminant non-A non-B hepatitis is often accompanied by a serious icterus.

The time factor allows a certain prognostic conclusion. Paradoxically, the group of patients in whom encephalopathy develops most rapidly has the highest chance of spontaneous remission (Gimson 1986, Benhamou 1991). Thus a distinction is made between hyperacute, acute and subacute liver failure (O'Grady 1993). Hyperacute liver failure is used to describe patients in whom encephalopathy begins within 8 days of the onset of icterus. With respect to the etiology, paracetamol poisoning and sometimes acute hepatitis A and B are most likely to belong to this group. Acute liver failure includes patients with a time span of eight to twenty-eight days between icterus and encephalopathy. Most liver failures of viral etiology present in this way. In the case of subacute liver failure, encephalopathy occurs with a latency of four to twenty-six weeks. Most patients of this group have a so-called non-A non-B hepatitis where no viral agent can be identified.

Over 50% of cases of acute liver failure in North American and European centers progress like, and have the clinical picture of, an acute viral hepatitis, although in many cases no specific viral hepatitis pathogen can be identified (Fagan and Harrison 1994). In most series, hepatitis B is the most common viral hepatitis pathogen which can cause an acute liver failure, followed by non-A and non-B and hepatitis A. This applies particularly in France, where 46% of all patients with acute liver failure are HBV-positive. In Japan the figure is as high as 62%. Due to the low prevalence of HBV infections in Great Britain, in the United Kingdom, non-A non-B hepatitis is the most common viral cause of an acute liver failure. Hepatitis C plays a lesser role in the large centers of the Western world (Sallie et al 1994) although a few well-documented case reports of fulminant hepatitis C have been published (Theilmann 1992).

Of 342 cases of acute liver failure which were admitted to King's College, London from 1993—1994 with grade III or IV encephalopathy, 250 cases involved a paracetamol (acetaminophen) poisoning. A viral genesis was assumed with 44 patients (hepatitis A n=8, hepatitis B n=8, non-A, B, C, D, E n=28). Rare causes were Morbus Wilson, pregnancy gestosis, lymphoma/malignant transformation, sepsis, Budd-Chiari syndrome, ischaemic hepatitis and reactions to drugs (e.g. cyproterone, non-steroidal antiphlogistics, chloroquine, rifampicin, isoniazid, halothane, flucloxacillin).

At the time of the admission of the patient, the decisive liver damage has already occurred. The histological examination of the liver shows at this point necrosis zones and—depending on the latency—also already regeneration zones. The clinical symptoms and the progression of the disease depend on the interplay of three factors: (1) the regeneration capacity of the liver; (2) the adverse metabolic consequences of a liver breakdown; and (3) the release of proinflammatory, partly toxic mediators from the necrotic liver. Characteristically, liver failure is followed by multiple organ failure.

The prognosis is decisively influenced by the presence of an encephalopathy with consecutive cerebral oedema. Patients with acute liver failure, whose encephalopathy does not progress beyond grade I–II have an excellent prognosis, whereas the patient group with grade III–IV has a considerably higher mortality. Usually, 80% of patients with a grade IV encephalopathy develop a cerebral oedema (O'Grady et al. 1988). The pathogenetic factors which lead to hepatic encephalopathy and cerebral oedema are still little researched. A distinction can be made between vasogenic factors which lead to an extracellular oedema due to the damaged blood-brain barrier, and cytotoxic mediators which lead to intracellular oedema. The latter includes benzodiazepine agonists, a modified gamma amino butyric acid status, an increased concentration of aromatic amines, ammonia and mercaptans. Basile et al. (1991) were able to show increased concentrations of 1,4-benzodiazepines in the brains of patients with acute liver failure.

The clinical signs which result from the increased intracranial pressure are coma, systemic hypertension, abnormal pupil reflexes and impairment of the brain stem reflexes. The increased intracranial pressure further causes a decreased cerebral blood supply (Almdal et al. 1989, Sari et al. 1990) with consecutive cerebral ischaemia and sometimes epileptiform activity.

Hypoglycemia occurs early in the clinical progression and is the result of increased circulating insulin with simultaneously impaired gluconeogenesis and reduced glucogenic degradation. In addition a hypophosphataemia is also observed early on. The commonly found metabolic acidosis can be explained by the restricted lactate metabolism of the liver and by tissue hypoxia with increasing peripheral lactate formation (Bihari, 1985).

Infections are a common complication of acute liver failure, and it must be accepted that in liver failure, primarily the function of neutrophil leukocytes and the Kupffer cells and also opsonization is restricted.

This leads to an impaired clearance of endotoxins and a translocation of bacteria through the gut mucosa barrier.

In the King's College series, bacterial infections were identified in 80% of patients with acute liver failure, wherein in terms of cultivation, *staphylococcus aureus* proved to be the most common pathogen (Rolando et al 1990). Fungal infections, mostly *Candida albicans,* become increasingly important in the later progression of the disease (Rolando 1991).

A further characteristic cardinal symptom of acute liver failure is coagulopathy. The prothrombin time correlates well with the severity of the liver damage. As the coagulation factor V has the shortest half-life, it is the most sensitive parameter for coagulopathy. This can be explained however not only by a restricted synthesis of coagulation factors. In addition, within the framework of a disseminated intravasal coagulation (DIC), an increased peripheral oxygen consumption occurs (O'Grady et al. 1986). The platelet function is also restricted: thrombocytopenias and restricted aggregation in the case of acute liver failure have been described.

Orthotopic liver transplantation is the therapy of choice in the case of fulminant and chronic liver failure. However we are increasingly confronted with a marked shortage of organs. According to United States data, a patient is listed for a transplantation every 30 minutes, whereas a donor is registered only approximately every 2 hours. The situation is also similar in Europe. In 1996, 973 liver transplantations were carried out in Europe, whereas in the same period, 1393 new patients were registered on the waiting list for a liver transplantation. In 1996, 200 (12%) of the patients on the waiting list for a liver transplantation died.

A liver transplantation is often unavoidable in the case of acute liver failure because after fulminant infectious hepatitis or intoxication (amanita, acetaminophen, tetrachlorocarbon, etc.), the liver does not regenerate quickly enough. Mortality without transplantation is given as between 70%–90% in the literature. Even though clinical criteria for the indications for liver transplantation have been formulated by several groups, it can be extremely difficult to specify the correct transplantation time or to obtain a suitable organ in time. A temporary liver replacement would make it possible for the patient to survive the phase of liver regeneration without the transplantation which is costly and, due to the shortage of organs, often not available in time. Life-long immunosuppression with all its side effects could then also be avoided. As temporary liver replacement, a plurality of different procedures have been tested: haemodialysis, haemoadsorption with activated charcoal, affinity chromatography for the removal of metabolic products and many other techniques have not been widely accepted. By far the most promising development is that of the "bioartificial" liver. Because of the complexity of the metabolic and physiological functions of the liver, this extracorporal liver replacement system contains living hepatocytes. As human liver cells are not available in sufficient quantity and can be multiplied only inadequately in culture, either hepatoma cell lines or xenogenic hepatocytes from pigs were used. This is only possible for the patient with corresponding safety if patient plasma or blood do not come into direct contact with the liver cell compartment. Only thus can undesired immune reactions and infections be prevented. A semi-permeable membrane therefore separates blood/plasma on the one hand from the hepatocytes on the other and nevertheless makes possible the necessary exchange of substances. Individual case reports on the continuous use of such a bioartificial liver in the case of patients with fulminant liver failure gave reason to hope at first. However, controlled clinical studies with these sometimes commercially available systems showed no advantage in respect of survival for patients with acute liver failure.

SUMMARY OF THE INVENTION

It is accordingly an object of the invention to provide a bioartificial device, which overcomes the above-mentioned disadvantages of the heretofore-known devices and methods of this general type and which enables a cultivation of cells, in particular on microscopically small carrier particles (microcarriers), and which is suitable for use as an extracorporal system under the following conditions:
 Sufficient space for the cells contained in a suspension (for example $2\times10^{10}$ liver cells);
 Maximum exchange surface of the dividing wall between the cell culture and the throughflow chamber for the body substance;
 Exchange of substances up to a maximum mass of approx. 100,000 to 120,000 dalton;
 Elimination of gas bubbles.
In addition, the following characteristics are preferable:
 Adherence to microgravity conditions, i.e. extremely low shear forces and turbulences;
 Continuous supply of oxygen-saturated nutrient medium; and
 Continuous assessment of cell quality and condition of the nutrient medium.

With the foregoing and other objects in view there is provided, in accordance with the invention, a bioartificial device, comprising:

a reactor vessel formed with a cell culture chamber, a first throughflow chamber for a nutrient medium separated from said cell culture chamber by a semipermeable wall, and a second throughflow chamber for a body substance separated from said cell culture chamber by a semipermeable wall. According to the invention, at least one of said first and second throughflow chambers is formed by a tube of semi-permeable material helically disposed in said cell culture chamber.

In other words, a device according to the invention has at least one of the two throughflow chambers formed by a tube, made of a semi-permeable material, helically coiled in the cell culture chamber. This configuration creates a maximum exchange surface with a very simple construction, as the throughflow chamber is almost completely surrounded by the cell culture provided in particular in the form of a suspension. In contrast to reactors in which several straight throughflow chambers arranged parallel to one another are provided in the form of flat slits, hollow fibres or similar, the device according to the invention has the advantage that instead of several parallel connections for inflow and out-flow only a single connection need be provided between the tube and the inflow and/or the outflow, the tube having the necessary large exchange surface on account of the helical coil.

Because, in use as a bioartificial liver, the exchange surface between plasma/blood and the cell suspension should be substantially larger than the exchange surface between the nutrient medium and the cell suspension, it is furthermore preferably provided that the throughflow chamber for the body substance is formed by a tube coil arranged near the outer wall of the reactor vessel, and the throughflow chamber for the nutrient medium is arranged centrally in the reactor vessel inside the tube coil. In a first preferred version, the throughflow chamber arranged centrally in the reactor vessel can likewise be formed by a helically arranged tube made from a semi-permeable tube. The two tube coils can therefore be arranged coaxially inside one another. In this version, the throughflow chamber for the nutrient medium also has a large exchange surface.

In a second preferred embodiment of the invention, the central throughflow chamber for the nutrient medium is cylindrical and has a wall comprising a semi-permeable membrane. In this version, the semi-permeable membrane is preferably composed of a nitrocellulose as is also used for membrane filters, and here, by selecting the pore size, the transfer rates between the nutrient medium and the cell culture chamber can be better matched to its requirements. As such nitrocellulose membranes are not self-supporting, it is preferably provided that the membrane is supported on a wire mesh.

For use as a bioartificial liver, a nitrocellulose membrane with a pore size of 0.3 µm has proved particularly favourable which has a transfer rate of 33 ml/min per square centimetre and a pressure difference of 1 bar between the cell culture chamber and the throughflow chamber for the nutrient medium.

It is an advantage both for supplying the cells with the nutrient medium and for the exchange of substances with the body substance if each throughflow chamber is allocated to a support driven in rotation. The rotation of the chamber leads to a type of weightless state in which cells do not lie in layers on top of one another but are kept floating in the suspension by the stirring effect and are supplied more uniformly and better with the nutrient medium. Preferably the support of the throughflow chamber through which the nutrient medium flows is connected to a central drive shaft and the support of the tube coil through which the body substance flows is connected to a driven flange of the reactor vessel which is housed rotatable on the central drive shaft.

The or each tube is preferably composed of a polyvinylidene difluoride (PVDF) and at least the outer tube has a pore size corresponding to approximately 100,000 dalton. If both throughflow chambers are formed by tube coils, the throughflow directions of the nutrient medium and the body substance are preferably opposed.

The rotation speed is variable and should be set at between 20 and 40 revolutions per minute. The two supports are preferably driven separately so that for example the inner support can be driven faster in order to counteract a gradient between outer and inner walls. The volume of the inside of the cylinder is preferably approximately one liter. It is filled gas-bubble-free with a suspension culture of hepatocytes. In this case, the cell suspension contains approximately $2 \times 10^{10}$ cells, which corresponds approximately to the yield of a pig liver. An outer tube coil for plasma/blood preferably covers a surface of approx. 4.5 $m^2$. The bioreactor is kept at a temperature of 37° C. by an incubator, a water jacket, an outer heating coil or similar. Because of the continuous supply of oxygen from the oxygen-saturated nutrient medium saturated with oxygen through the wall of the inner throughflow chamber and the plasma and/or blood preferably enriched with oxygen through the wall of the outer tube, an average life of the liver cells of 20 days can be achieved, wherein a very good to adequate functionality was found over at least 14 days.

The reactor vessel, in a preferred embodiment, is cylindrical and has a horizontally arranged axis.

The feed and discharge connections or the or each throughflow chamber can be arranged in the two end surfaces of the reactor vessel. They are preferably arranged on the same side, wherein the tube can be returned at the end of the coil in different ways. A first possibility provides for a second helical coil, a second possibility a straight reflux section and a preferred third variant a rigid reflux pipe which can run in particular in the central shaft.

Alternatively the bioartificial device can have stationary connections and fixed throughflow chambers. In this case the reactor vessel is housed rotatable on a fixed bearing block, to which the throughflow chambers are attached, and provided with an external drive. A gentle stirring effect in the cell culture suspension can be achieved in that the in particular box-like reactor vessel has at least one wing or similar projecting between the tube coils and/or throughflow chambers, which rises from the vessel floor.

Other features which are considered as characteristic for the invention are set forth in the appended claims.

Although the invention is illustrated and described herein as embodied in a bioartificial device for storing, cultivating, and/or multiplying cells, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
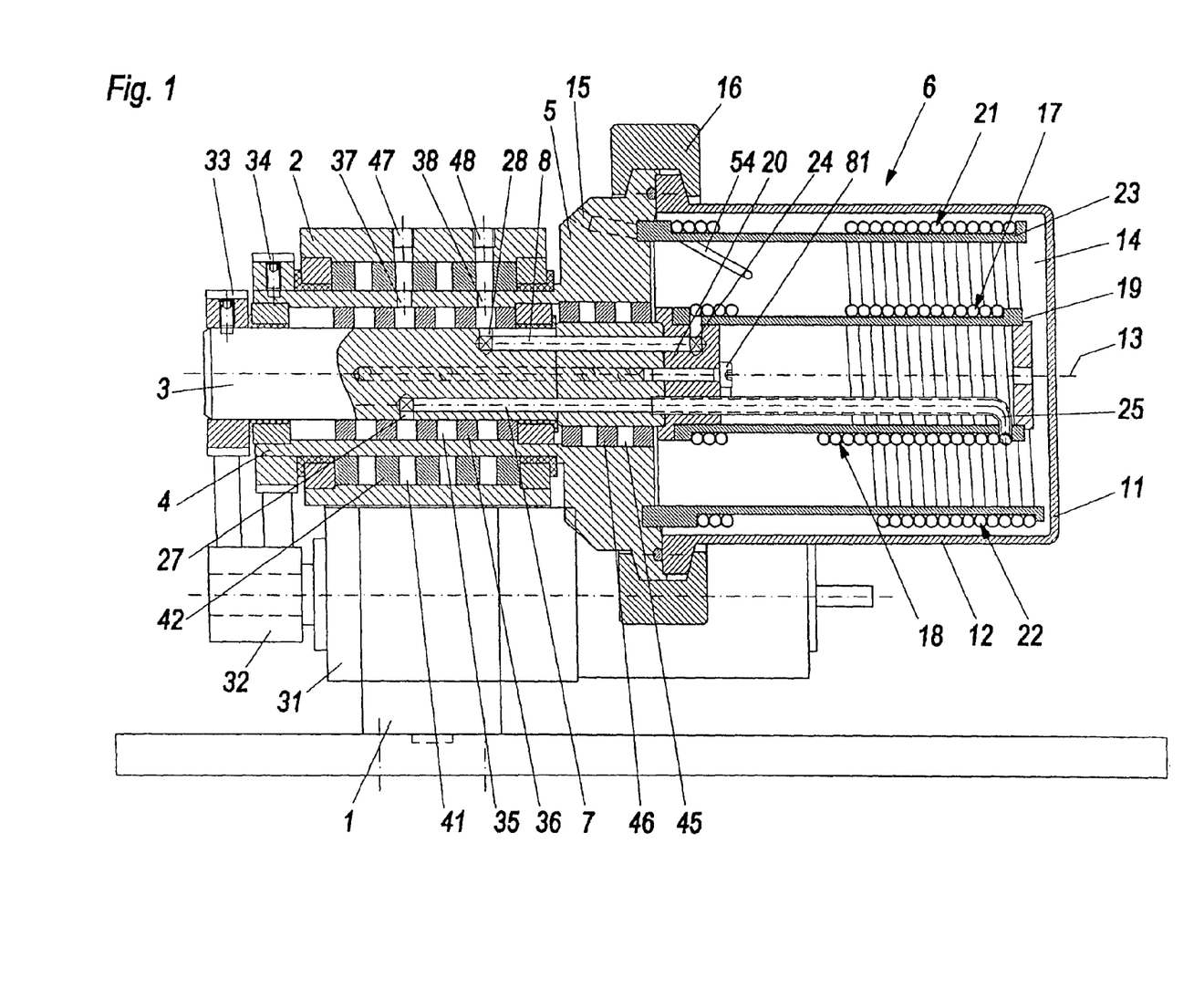
FIG. 1 is an axial section through a first embodiment of a bioartificial device with liver function along the line I—I of FIG. 3.
Figure 2:
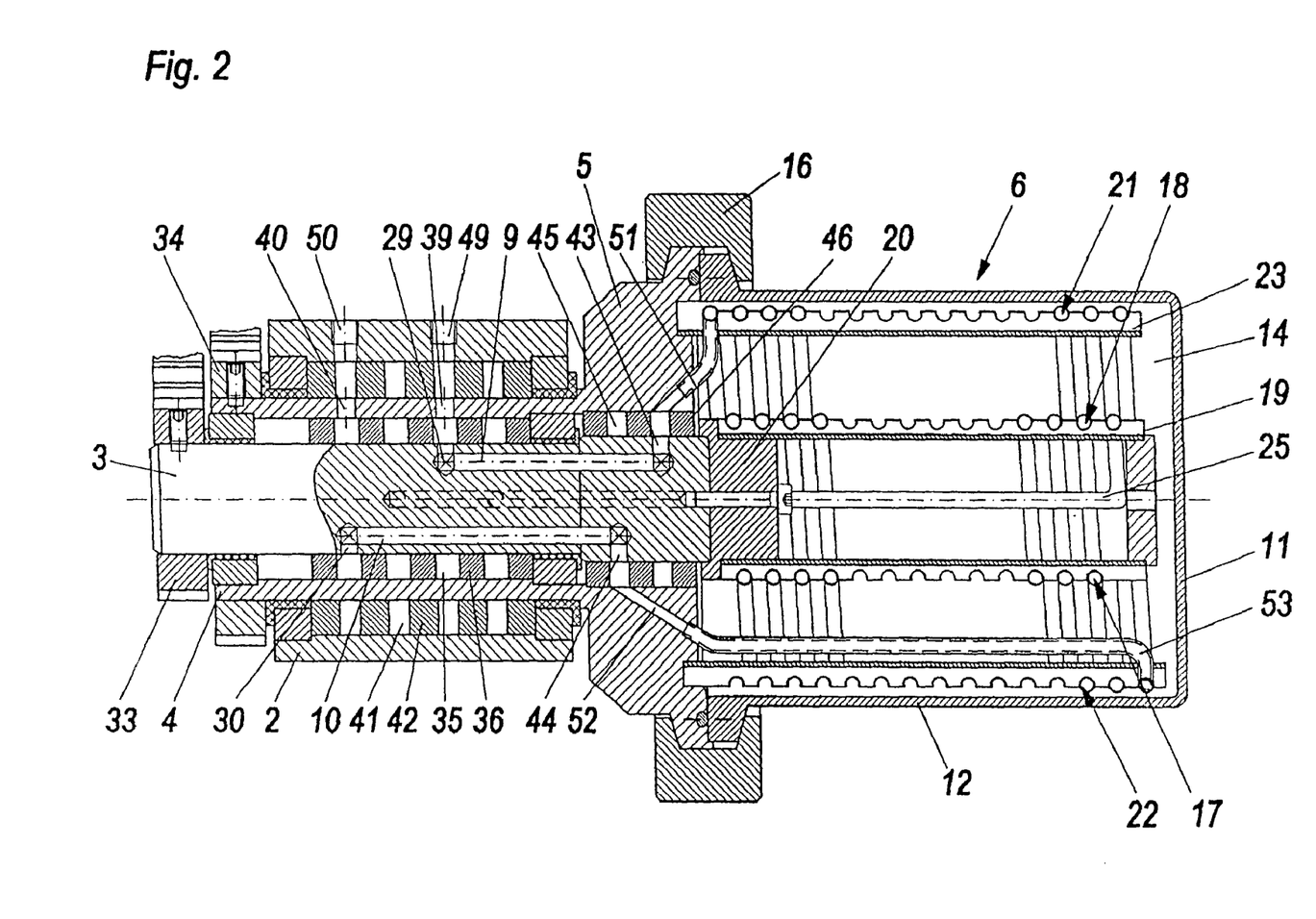
FIG. 2 is an axial section, shifted by 90°, through the bioartificial device along the line II—II of FIG. 3.
Figure 3:
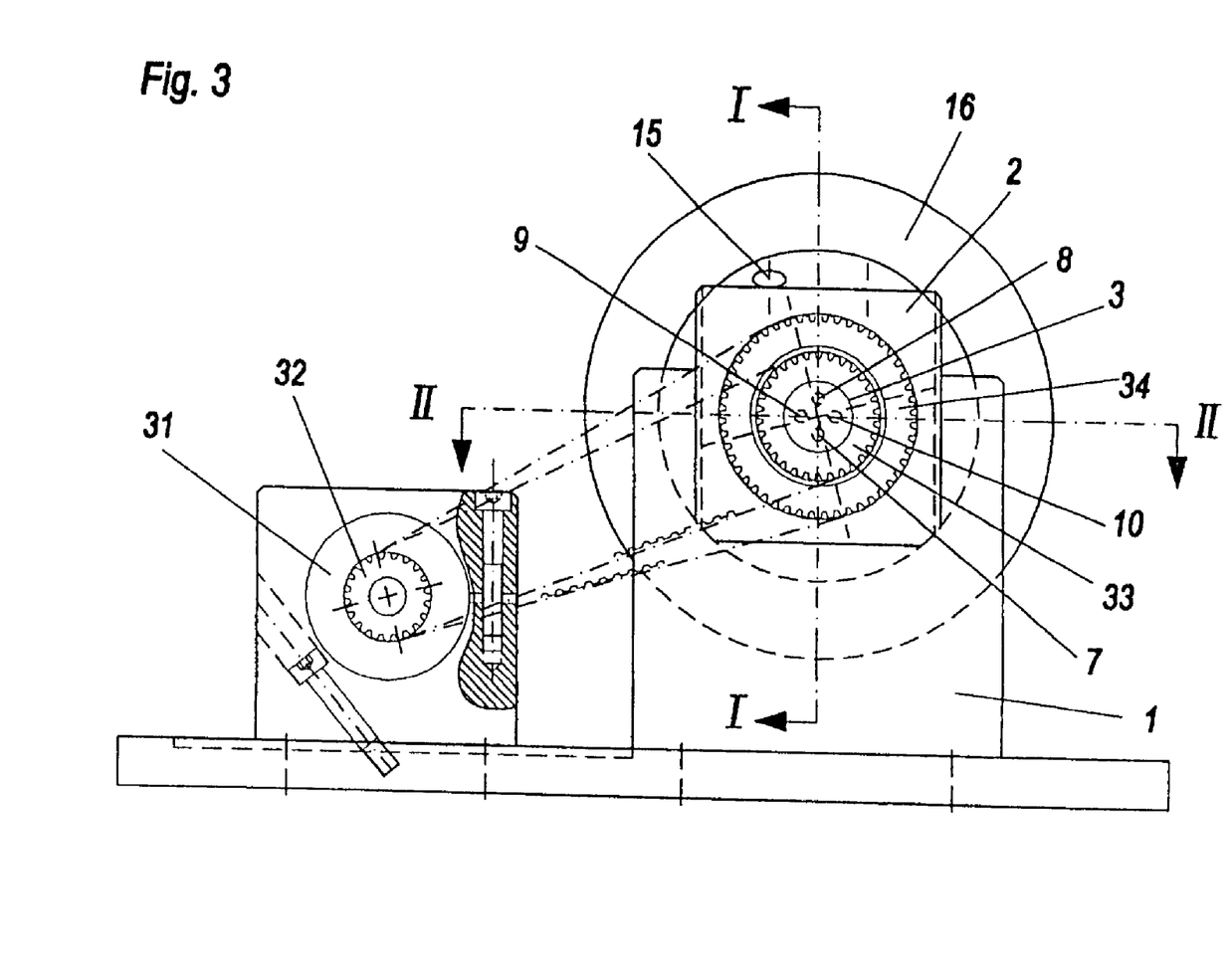
FIG. 3 is an end view thereof.

Referring now to the figures of the drawing in detail and first, particularly, to FIGS. 1–3 thereof, there is shown a bioartificial device with a reactor vessel 6 that is disposed in a base frame 1 rotatable about a horizontal axis 13. A bearing block 2 is inserted vertically into the base frame 1, in which a hollow-cylindrical outer drive shaft 4 is housed which has an end-side flange 5. The flange 5 and a casing 11, connected to same via an easily releasable locking ring 16 and made in particular of transparent material form the reactor vessel 6. A central drive shaft 3 is housed and rotatably supported in the hollow-cylindrical drive shaft 4. Both drive shafts 3, 4 are provided with drive transmission elements 33, 34, for example toothed wheels, belt pulleys or similar which are connected via a corresponding traction mechanism to a drive element 32 of a motor 31. The drive transmission element 34 preferably has a larger outer diameter so that the speed of the drive shaft 4 is less than the speed of the drive shaft 3.

The reactor vessel 6 has a cell culture chamber 14 which is accessible via at least one inspection opening 15 developed in the flange 5. A sampling of the cell culture and likewise a removal or supply can take place via this inspection opening in order to equalize possible pressure changes in the reactor vessel 6. A pipe or tube section 54 preferably extends from the or an inspection opening 15 into the inside of the cell culture chamber 14 in order to make possible a sampling from an area not situated by the edge.

A throughflow chamber 17 for a nutrient medium and a throughflow chamber 21 for a body substance, in particular plasma and/or blood leads through the cell culture chamber 14. The throughflow chambers 17 and 21 are arranged separated from one another and each developed in a tube which is composed of a semi-permeable material, in particular a polyvinylidene difluoride (PVDF), the pore size of which corresponds at most to approximately 100,000 dalton. The throughflow chamber 17 for the nutrient medium is formed by the tube coil 18 which is helically coiled onto a support 19 which has several support bars receiving the coils. The support 19 rises at the end from a connection element 20 which is attached by means of a screw 81 to the central drive shaft 3. The support 19 and the tube coil 18 therefore rotate with the drive shaft 3. The tube forming the throughflow chamber 21 for plasma and/or blood is likewise helically coiled in the form of a tube coil 22 onto two to eight support bars which form the support 23. The support bars of the support 23 rise from the flange 5 near the outer wall 12 of the reactor vessel 6, which flange is provided on the preferably more slowly rotating outer drive shaft 4.

Both tube coils 18, 22 are arranged in the cell culture chamber 14, wherein the horizontal rotational axis 13 and the preferred speed difference between the two tube coils produce a slightly gentle stirring effect in the cell culture by which the exchange of substances between the nutrient medium in the central tube and the cell culture and also between the plasma and/or blood in the outer tube and the cell culture is favoured. The helical arrangement of the two tubes furthermore results in a very large exchange surface between the individual media. The tube coils can be arranged on the supports 19, 23 either in contact (FIG. 1) or spaced apart (FIG. 2). Where they are arranged in contact, a higher number of coils results in a greater overall length, whereas when they are spaced apart the exchange can take place over the whole circumference of the tube, as the reciprocal covering in the contact area of the coils is dispensed with.

The inflow of the nutrient medium and the plasma and/or blood into the tube coils 18, 22 and its reflux each take place via the central drive shaft 3 in flow channels separated from one another. Connections 47, 48, 49, 50 are provided at the bearing block 2 which are in flow connection with radial bores 27, 28, 29, 30 of the central drive shaft 3. Outer ring channels 41 are provided for each inflow and/or reflux between the inner wall of the bearing block 2 and the outer drive shaft 4, which ring channels are delimited by axially spaced separator rings 42 and each of which creates flow connections between the connections 47, 48, 49, 50 and radial bores 37, 38, 39, 40 of the rotating outer drive shaft 1. Inner ring channels 35 are provided for each inflow and/or reflux between the inner wall of the outer drive shaft 4 and the central drive shaft 3, which ring channels are delimited by axially spaced separator rings 36 and which create the respective flow connection between the radial bores 37, 38, 39, 40 of the outer drive shaft 4 and the bores 27, 28, 29, 30 of the faster-rotating central drive shaft 3.

The central drive shaft 3 contains four parallel flow channels 7, 8, 9, 10. Of these the flow channel 7 is extended by an extension pipe 25 which projects into the casing 11 and the radially bent end of which is connected to the first end, opposite the flange 5, of the tube coil 18. The flow channel 8 is extended into a connection element 20 and ends in a radial entry bore 24 to which the second end, near to the flange, of the tube coil 18 is connected. Nutrient medium for supplying the cell culture can thus flow via the first connection 47 into the outer ring channel 41, through the bore 37 of the outer drive shaft 4 into the inner ring channel 35, through the bore 27 of the central drive shaft 3 in its first flow channel 7 and through the extension pipe 25 into the tube coil 18. The circulating nutrient medium flows out of the tube coil 18 through the inlet 24, the second flow channel 8 and the radial bore 28 of the central drive shaft 3 into the associated inner ring channel 35 and also through the bore 38 of the outer drive shaft 4 and the associated outer ring channel 41 to the second connection 48 of the bearing block 2.

The flow channels 9, 10 of the central drive shaft 3 are connected via inner radial bores 43, 44 to ring channels 45 which are delimited by separator rings 46 and arranged between the central drive shaft 3 and the flange 5 of the outer drive shaft 4. The flange 5 has channels 51, 52 which lead into the area of the outer support 23. The tube coil 22 is connected at the exit of the channel 51. An extension pipe 53 leads from the exit of the channel 51 to the free end of the support 23 at which the second end of the tube coil 22 is connected to the extension pipe 53.

Plasma and/or blood flows via the third connection 49 into the bioartificial device and passes through the associated outer ring channel 41 and the bore 39 of the outer drive shaft 4 into the associated inner ring channel 35, through the bore 29 of the central drive shaft 3 into the third flow channel 9, through the second, inner bore 43 at the end of the flow channel 9 into the associated ring channel 45 and finally through the channel 51 in the flange 5 to the outer tube coil 22, in which a purification of the plasma and/or blood takes place by the exchange of substances with the cell culture in the cell culture chamber 14. The treated plasma and/or blood flows through the extension pipe 53 and the channel 52 in the flange 5 into the associated ring channel 45, through the inner bore 44 of the central drive shaft 3 into its fourth flow channel 10, through the outer bore 30 of the central drive shaft 3 into the associated inner ring channel 35, and through the bore 40 of the outer drive shaft 4 and the associated ring channel 41 to the fourth connection 50 of the bearing block 2.

For the first filling or emptying, the bearing block 2 is removed from the base frame 1 so that the reactor vessel 6 can be placed upright, the axis 13 running vertically. After removal of the locking ring 16, the bearing block 2 with the flange 5 and the tube coils 18, 22 arranged on the two supports 19, 23 can be removed at the top. The used cell culture can be emptied or new cell culture poured into the casing 11. The unit comprising flange 5 together with the two tube coils 18, 22 and the bearing block 2 is placed on the casing 11 and sealed with the help of the locking ring 16 to the reactor vessel 6. The reactor vessel 6 can then be laid down and with the help of the bearing block 2 inserted in a horizontal position into the base frame 1.

In a preferred version, the casing 11 has a capacity of approximately one cubic decimetre and can house approx. $2 \times 10^{10}$ hepatocytes suspended in a medium. The speeds of the two drive shafts 3, 4 lie in particular between 20 and 40 revolutions per minute, the speed of the central drive shaft 3 corresponding for example to one and a quarter times the speed of the outer drive shaft 4. In this case, the speeds are thus 20 and 30 revolutions to 25 and 37.5 revolutions per minute.

Figure 4:
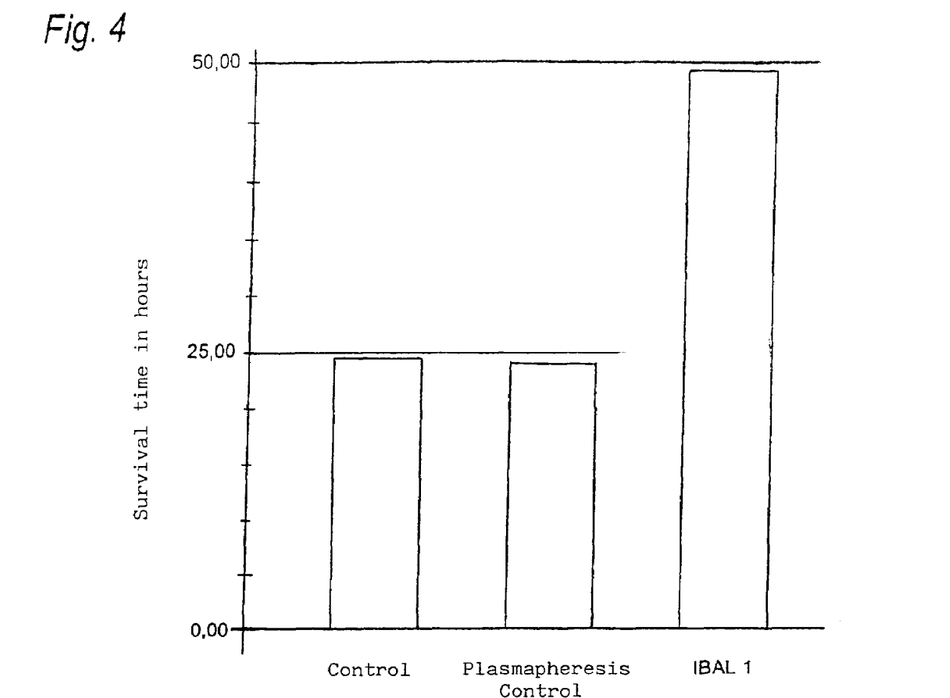
FIG. 4 is a bar graph charting the survival times of three laboratory animals.
Figure 5:
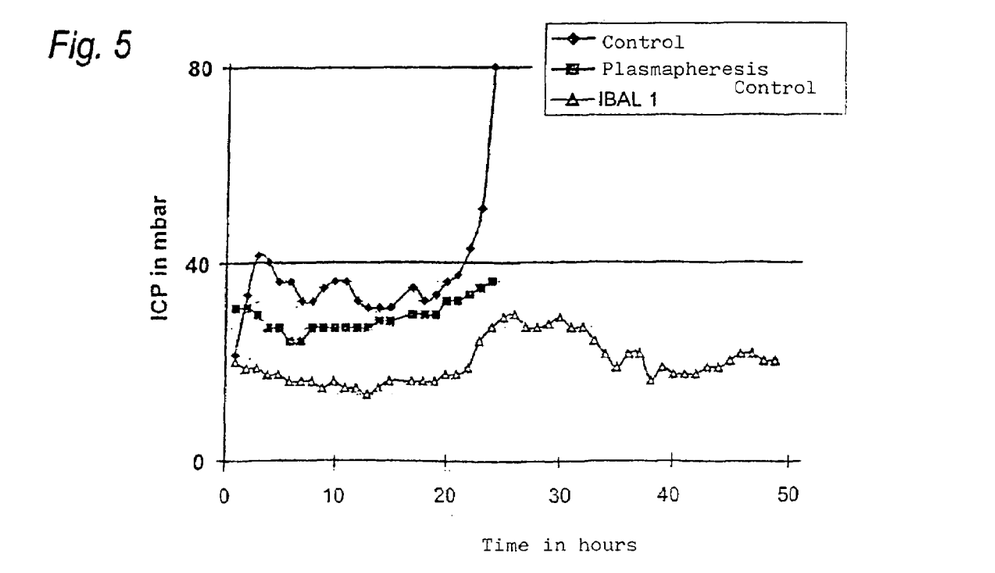
FIG. 5 is an associated diagram showing the intracranial pressure pattern of the laboratory animals.

FIGS. 4 and 5 show the result of a laboratory test in which, in the case of three German landrace pigs each of approx. 30 kg live weight, the survival time was established in a surgically induced model of acute liver failure. Acute liver failure was induced by an 80% liver resection with subsequent one-hour clamping of the hilus of the remaining liver. Furthermore, inter alia the intracranial pressure (ICP) was monitored. As a plasmapheresis is also used to treat acute liver insufficiency, the following procedure was used: One of the three animals remained untreated (control), with a second animal, plasma was separated out of the blood in a plasmapheresis device and reinfused as whole blood without further manipulation (plasmapheresis control). With the third animal, plasma was likewise separated out of the blood in a plasmapheresis device, and then passed through a bioartificial device with the specification described above. The treated plasma was mixed in turn with the previously separated remaining blood and returned (IBAL 1).

FIG. 4 shows that the control animal and the plasmapheresis control animal each survived for almost 24 hours. On the other hand, the third animal, the plasma of which was purified and/or regenerated in the bioartificial device according to the invention, lived for almost 50 hours, wherein the cause of death, as FIG. 5 shows, was not an increase in the intracranial pressure (ICP). In contrast, the intracranial pressure increased greatly in the case of the control animal, less so, but still clearly in the case of the plasmapheresis control animal.

Figure 6:
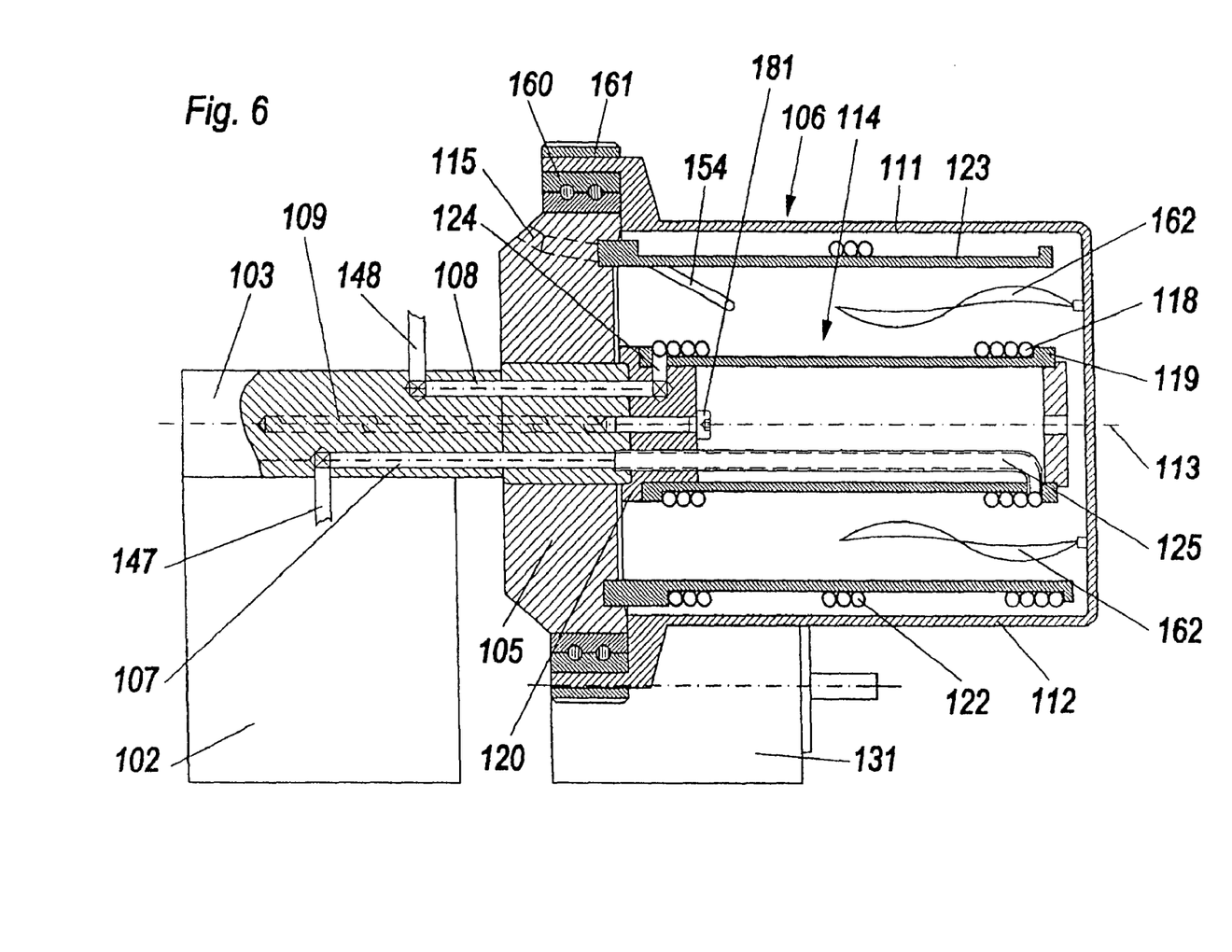
FIG. 6 is an axial section similar to FIG. 1 of a second embodiment of the bioartificial device with liver function according to the invention.

In the embodiment according to FIG. 6, a central cylindrical holding element 103 is removably arranged in a bearing block 102. The holding element has the shown connections 147, 148 via which nutrient medium can be supplied and removed, as well as two further connections via which blood and plasma can be supplied and removed. The connections 147, 148 open into flow channels 107, 108 which extend parallel to the axis 113. A flange 105 is mounted on the holding element 103 with a thick roller bearing 160 on which a casing 111 of a reactor vessel 106 is rotatably housed. The casing 111 is provided on the outside of the wall 112 with a toothed rim 161 and is rotatably connected to a motor 131 via a drive transmission element. The flange 105 and the casing 111 of the reactor vessel 106 contain a cell culture chamber 114 into which two stirring elements 162 project from the base of the casing 111, which support the gentle blending, caused by the rotation of the housing wall 112, of the contents of the cell culture chamber 114.

The flow channel 108 ends in a connecting element 120 which has a radial bore 124 and is fixed by means of a screw 181 to flange 105 and/or the holding element 103. The flow channel 107 is extended beyond the connecting element 120 by an extension pipe 125. A tube 118 coiled helically on bars of a support 119 is connected on one side to the extension pipe 125 and on the other side to the radial bore 124, wherein the tube coil projects centrally as an extension of the holding element 103 into the rotating casing 111.

A second tube 122 helically coiled on bars of a support 123 serves as a throughflow chamber for blood and plasma and is connected via channels, not shown, running in the flange 105 to flow channels in the holding element 103, of which the flow channel 109 is indicated by a broken line. The reactor vessel 106 has an inspection opening 115 which is connected to the cell culture chamber 114 via an inner tube or pipe section 154.

Figure 7:
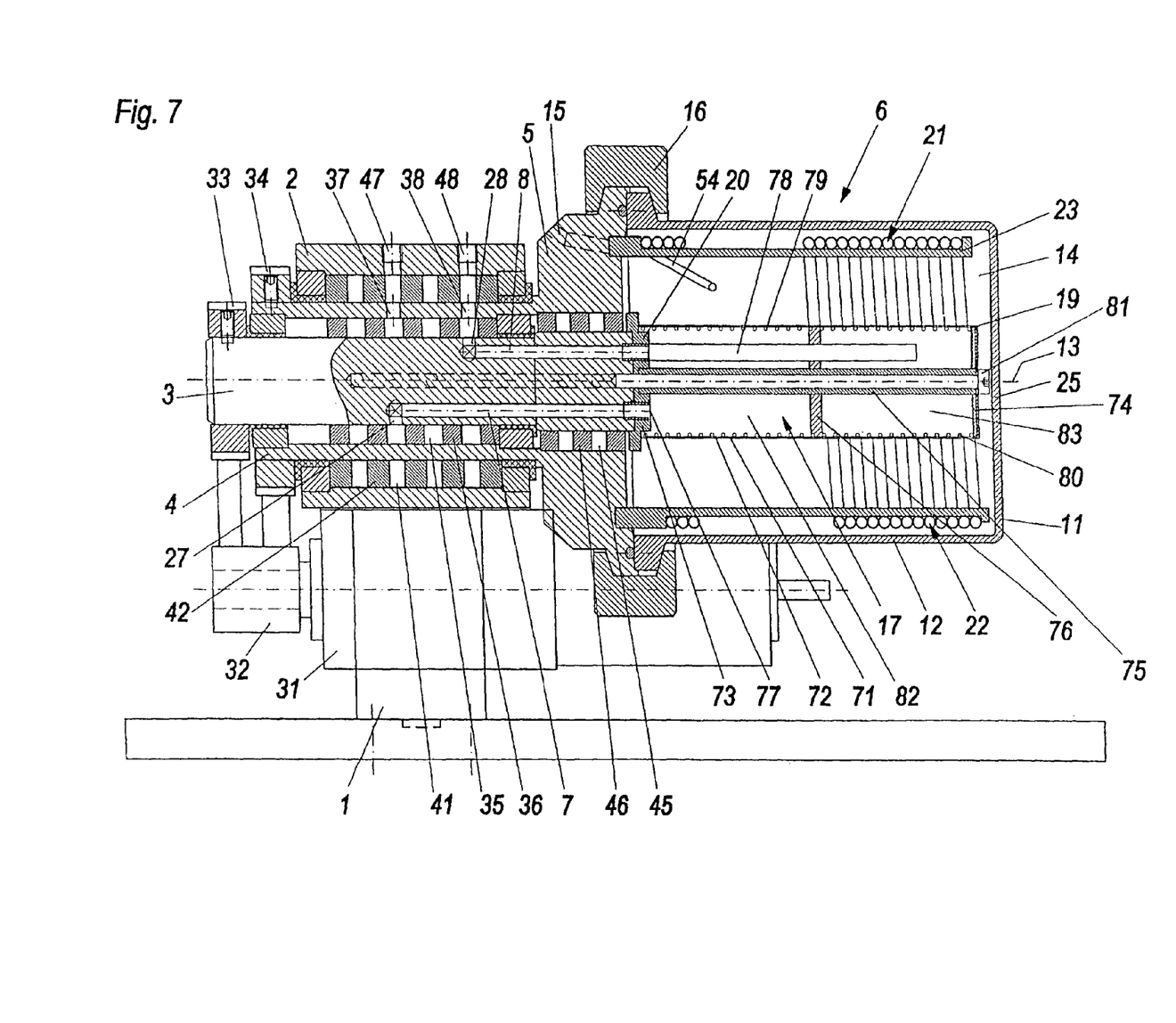
FIG. 7 is an axial section similar to FIG. 1 of a third embodiment of the bioartificial device according to the invention.

A further embodiment of the invention is shown in FIG. 7 in which the throughflow chamber 21 for plasma and/or blood is again developed in the form of a tube coil 22 which is arranged near the outer wall 12 of the reactor vessel 6. The throughflow chamber 17 for the nutrient medium is formed in this version on the other hand by a cylindrical fitting, divided into two chambers 82, 83, which is attached by means of a screw 81 to the central drive shaft 3 and has a wall made of a semi-permeable membrane 71. The fitting comprises two end plates 73, 74 and an approximately central dividing wall 76 which are connected by a central spacer 75. The semi-permeable membrane 71 is supported by a wire mesh 72 which is reinforced by at least one helical spring 79, 80 per chamber 82, 83. The semi-permeable membrane 71 is produced in particular from nitrocellulose and has a pore size of 0.3 µm. The wire mesh 72 has for example a mesh size of 45 µm and is composed of a corrosion-resistant metal or of a suitable plastic.

The end plate 73 corresponds to the connecting element 20 of FIGS. 1 and 2 which connects to the end surface of the central drive shaft 3. The end plate 73 has an opening 77 aligned with the flow channel 7 and opening into the first chamber 82. Into the second chamber 83 there projects a pipe section 78 which extends parallel to the axis 13 of the end plate 73, and serves for the reflux of the nutrient medium out of the second chamber 83 into the flow channel 8 of the central drive shaft 3.

In the embodiment according to FIG. 7—as in FIGS. 1 to 3—both throughflow chambers 17, 21 are arranged rotatable in the casing 11 of the reactor vessel 6 and are driven via the drive shafts 3, 4 in the manner described in FIGS. 1 to 3. It is however likewise possible, in the version according to FIG. 6 with stationary throughflow chambers and driven casing 111, to develop the throughflow chamber for the nutrient medium as a cylindrical fitting with a semi-permeable nitrocellulose membrane 71.

We claim:

1. A bioartificial device, comprising:
   a reactor vessel having a first end and a second opposite end, said reactor vessel being formed with a cell culture chamber, a first throughflow chamber for a nutrient medium separated from said cell culture chamber by a semipermeable wall and including an inlet end adjacent said first end of said reactor vessel and an outlet end adjacent said second end of said reactor vessel, and a second throughflow chamber for a body substance separated from said cell culture chamber by a semipermeable wall and including an inlet end adjacent said first end of said reactor vessel and an outlet end adjacent said second end of said reactor vessel, said first throughflow chamber for the nutrient medium being centrally disposed and being cylindrical with a wall including a semi-permeable membrane, and said second throughflow chamber being formed by a tube of semi-permeable material helically disposed in said cell culture chamber;
   said inlet ends of said first and second throughflow chambers being in fluid communication with feed connections disposed on said first end of said reactor vessel and said outlet ends of said first and second throughflow chambers being in fluid communication with discharge connections disposed on said first end of said reactor vessel with tubes guided through said reactor vessel and extending from said discharge connections to said outlet ends of said throughflow chambers.

2. The device according to claim 1, wherein said rector vessel is formed with an outer wall, said second throughflow chamber is a tube coil arranged near said outer wall, and said first throughflow chamber is disposed centrally in said reactor vessel inside said tube coil.

3. The device according to claim 1, wherein said semi-permeable membrane is supported on a wire mesh.

4. The device according to claim 1, wherein at least one of said first and second throughflow chambers is supported on a driven carrier.

5. The device according to claim 4, which comprises a central drive shaft connected to said driven carrier for said throughflow chamber for the nutrient medium.

6. The device according to claim 4, wherein said reactor vessel is formed with a driven flange connected to said driven carrier of said tube coil through which the body substance flows, and said driven flange is rotatably supported on a central drive shaft.

7. The device according to claim 1, wherein each of said first and second throughflow chambers is supported on a driven carrier and said driven carriers have mutually different rotational speeds.

8. The device according to claim 1, wherein said reactor vessel is formed with a driven peripheral wall and each said throughflow chamber is disposed on a stationary support.

9. The device according to claim 8, which comprises at least one stirring element assigned to said driven peripheral wall and projecting between said first and second throughflow chambers.

10. The device according to claim 9, wherein said reactor vessel has a driven casing with a base, and said stirring element rises from said base.

11. The device according to claim 1, wherein said reactor vessel is a cylindrical vessel with a substantially horizontal axis.

12. The device according to claim 1, wherein said cell culture chamber is allocated at least one inspection and/or pressure-equalization opening.

13. The device according to claim 1, wherein said cell culture chamber is configured for liver cells.

14. The device according to claim 1, wherein said second throughflow chamber is configured for a body substance selected from the group consisting of plasma and blood.

15. A bioartificial device, comprising:
    a reactor vessel having a first end and a second opposite end, said reactor vessel being formed with a cell culture chamber, a first throughflow chamber for a nutrient medium separated from said cell culture chamber by a semipermeable wall and including an inlet end adjacent said first end of said reactor vessel and an outlet end adjacent said second end of said reactor vessel, and a second throughflow chamber for a body substance separated from said cell culture chamber by a semipermeable wall and including an inlet end adjacent said first end of said reactor vessel and an outlet end adjacent said second end of said reactor vessel, at least one of said first and second throughflow chambers being formed by a tube of semi-permeable material helically disposed in said cell culture chamber and at least one of said first and second throughflow chambers being supported on a driven carrier;
    said inlet ends of said first and second throughflow chambers being in fluid communication with feed connections disposed on said first end of said reactor vessel and said outlet ends of said first and second throughflow chambers being in fluid communication with discharge connections disposed on said first end of said reactor vessel with tubes guided through said reactor vessel and extending from said discharge connections to said outlet ends of said throughflow chambers.

16. The device according to claim 15, wherein said rector vessel is formed with an outer wall, said second throughflow chamber is a tube coil arranged near said outer wall, and said first throughflow chamber is disposed centrally in said reactor vessel inside said tube coil.

17. The device according to claim 15, wherein each of said first and second throughflow chambers is formed by a tube of semi-permeable material arranged helically in said cell culture chamber, and said two tube coils are disposed coaxially.

18. The device according to claim 15, which comprises a central drive shaft connected to said driven carrier for said throughflow chamber for the nutrient medium.

19. The device according to claim 15, wherein said reactor vessel is formed with a driven flange connected to said driven carrier of said tube coil through which the body substance flows, and said driven flange is rotatably supported on a central drive shaft.

20. The device according to claim 15, wherein each of said first and second throughflow chambers is supported on a driven carrier and said driven carriers have mutually different rotational speeds.

21. The device according to claim 15, wherein said reactor vessel is formed with a driven peripheral wall and each said throughflow chamber is disposed on a stationary support.

22. The device according to claim 21, which comprises at least one stirring element assigned to said driven peripheral wall and projecting between said first and second throughflow chambers.

23. The device according to claim 22, wherein said reactor vessel has a driven casing with a base, and said stirring element rises from said base.

24. The device according to claim 15, wherein said reactor vessel is a cylindrical vessel with a substantially horizontal axis.

25. The device according to claim 15, wherein said cell culture chamber is allocated at least one inspection and/or pressure-equalization opening.

26. The device according to claim 15, wherein said cell culture chamber is configured for liver cells.

27. The device according to claim 15, wherein said second throughflow chamber is configured for a body substance selected from the group consisting of plasma and blood.

28. A bioartificial device, comprising:
a reactor vessel having a first end and a second opposite end, said reactor vessel being formed with a cell culture chamber, a first throughflow chamber for a nutrient medium separated from said cell culture chamber by a semipermeable wall and including an inlet end adjacent said first end of said reactor vessel and an outlet end adjacent said second end of said reactor vessel, and a second throughflow chamber for a body substance separated from said cell culture chamber by a semipermeable wall and including an inlet end adjacent said first end of said reactor vessel and an outlet end adjacent said second end of said reactor vessel at least one of said first and second throughflow chambers being formed by a tube of semi-permeable material helically disposed in said cell culture chamber, said reactor vessel being formed with a driven peripheral wall, and each said throughflow chamber being disposed on a stationary support;
said inlet ends of said first and second throughflow chambers being in fluid communication with feed connections disposed on said first end of said reactor vessel and said outlet ends of said first and second throughflow chambers being in fluid communication with discharge connections disposed on said first end of said reactor vessel with tubes guided through said reactor vessel and extending from said discharge connections to said outlet ends of said throughflow chambers.

29. The device according to claim 28, wherein said rector vessel is formed with an outer wall, said second throughflow chamber is a tube coil arranged near said outer wall, and said first throughflow chamber is disposed centrally in said reactor vessel inside said tube coil.

30. The device according to claim 28, wherein each of said first and second throughflow chambers is formed by a tube of semi-permeable material arranged helically in said cell culture chamber, and said two tube coils are disposed coaxially.

31. The device according to claim 28, which comprises at least one stirring element assigned to said driven peripheral wall and projecting between said first and second throughflow chambers.

32. The device according to claim 31, wherein said reactor vessel has a driven casing with a base, and said stirring element rises from said base.

33. The device according to claim 28, wherein said reactor vessel is a cylindrical vessel with a substantially horizontal axis.

34. The device according to claim 28, wherein said cell culture chamber is allocated at least one inspection and/or pressure-equalization opening.

35. The device according to claim 28, wherein said cell culture chamber is configured for liver cells.

36. The device according to claim 28, wherein said second throughflow chamber is configured for a body substance selected from the group consisting of plasma and blood.

37. A bioartificial device, comprising:
a reactor vessel having a first end and a second opposite end, said reactor vessel being formed with a cell culture chamber, a first throughflow chamber for a nutrient medium separated from said cell culture chamber by a semipermeable wall and including an inlet end adjacent said first end of said reactor vessel and an outlet end adjacent said second end of said reactor vessel, and a second throughflow chamber for a body substance separated from said cell culture chamber by a semipermeable wall and including an inlet end adjacent said first end of said reactor vessel and an outlet end adjacent said second end of said reactor vessel, at least one of said first and second throughflow chambers being formed by a tube of semi-permeable material helically disposed in said cell culture chamber, said inlet ends of said first and second throughflow chambers being in fluid communication with feed connections disposed on said first end of said reactor vessel and said outlet ends of said first and second throughflow chambers being in fluid communication with discharge connections disposed on said first end of said reactor vessel with tubes guided through said reactor vessel and extending from said discharge connections to said outlet ends of said throughflow chambers.

38. The device according to claim 37, wherein said rector vessel is formed with an outer wall, said second throughflow chamber is a tube coil arranged near said outer wall, and said first throughflow chamber is disposed centrally in said reactor vessel inside said tube coil.

39. The device according to claim 37, wherein each of said first and second throughflow chambers is formed by a tube of semi-permeable material arranged helically in said cell culture chamber, and said two tube coils are disposed coaxially.

40. The device according to claim 37, wherein at least one of said first and second throughflow chambers is supported on a driven carrier.

41. The device according to claim 40, which comprises a central drive shaft connected to said driven carrier for said throughflow chamber for the nutrient medium.

42. The device according to claim 40, wherein said reactor vessel is formed with a driven flange connected to said driven carrier of said tube coil through which the body substance flows, and said driven flange is rotatably supported on a central drive shaft.

43. The device according to claim 37, wherein each of said first and second throughflow chambers is supported on a driven carrier and said driven carriers have mutually different rotational speeds.

44. The device according to claim 37, wherein said reactor vessel is formed with a driven peripheral wall and each said throughflow chamber is disposed on a stationary support.

45. The device according to claim 44, which comprises at least one stirring element assigned to said driven peripheral wall and projecting between said first and second throughflow chambers.

46. The device according to claim 45, wherein said reactor vessel has a driven casing with a base, and said stirring element rises from said base.

47. The device according to claim 37, wherein said reactor vessel is a cylindrical vessel with a substantially horizontal axis.

48. The device according to claim 37, wherein said cell culture chamber is allocated at least one inspection and/or pressure-equalization opening.

49. The device according to claim 37, wherein said cell culture chamber is configured for liver cells.

50. The device according to claim 37, wherein said second throughflow chamber is configured for a body substance selected from the group consisting of plasma and blood.

* * * * *